Aug. 26, 1975 R. G. JELLY Plant Pat. 3 774
ROSE PLANT
Filed Sept. 25, 1974
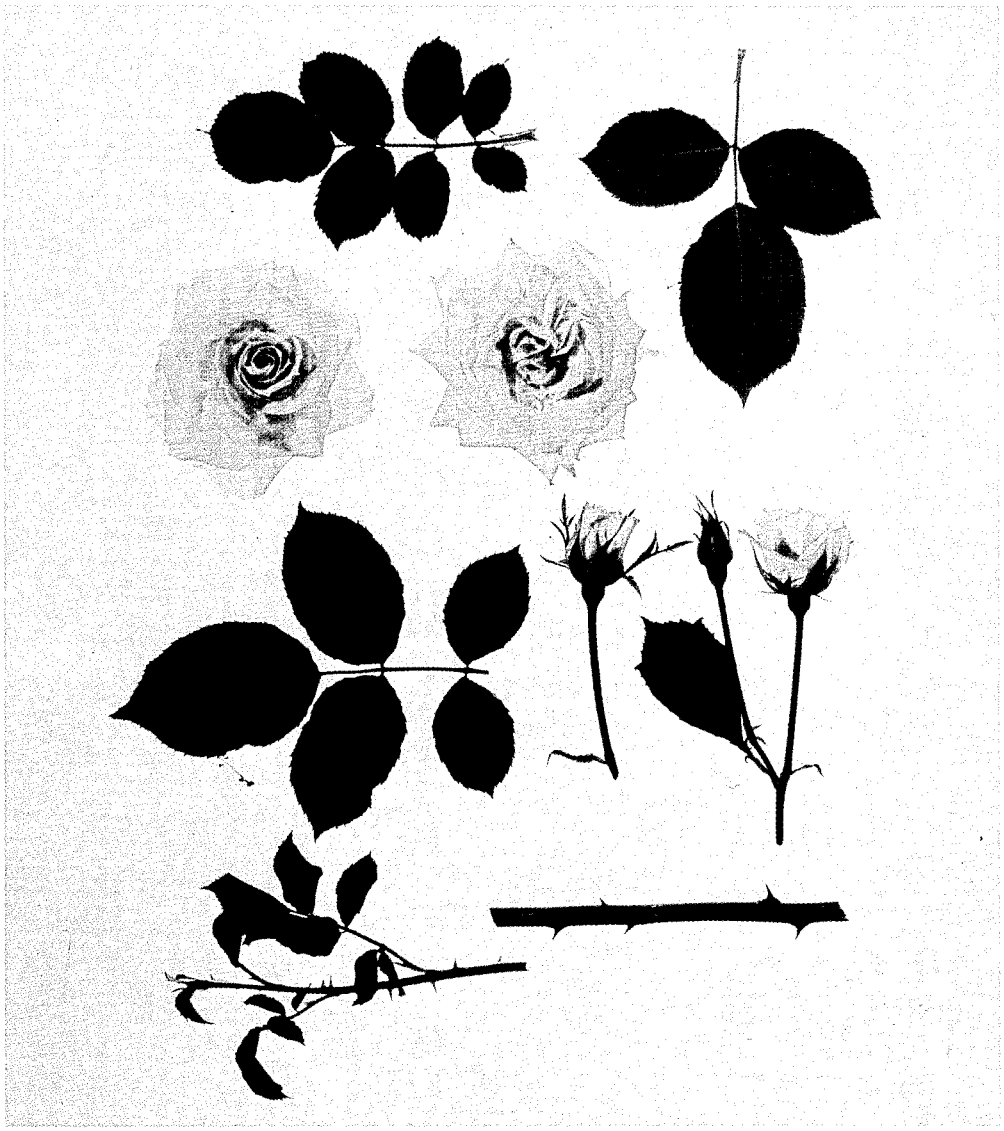

United States Patent

Plant Pat. 3,774

Patented Aug. 26, 1975

3,774

ROSE PLANT

Robert G. Jelly, Richmond, Ind., assignor to E. G. Hill, Inc., Richmond, Ind.

Filed Sept. 25, 1974, Ser. No. 509,276

Int. Cl. A01h 5/00

U.S. Cl. Plt.—26 1 Claim

ABSTRACT OF THE DISCLOSURE

A new variety of rose plant for greenhouse culture for cut flowers distinguished by its free and continuous production of shell pink blossoms of medium size, borne on moderately strong stems of medium length, and having an excellent vase life as cut flowers.

BACKGROUND OF THE INVENTION

This new variety of rose plant orginated as a seedling and resulted from breeding carried on by me at Richmond, Ind., with the object of improving the flower opening and finished flower form while retaining the color and plant renewal qualities of the pollen parent, Seventeen (Plant Pat. 1,765).

This plant is a seedling of an undisseminated seedling, identified as #19–64PS in my breeding stock, for which the pollen parent is Seventeen, the crossing having been made by me in September 1966 and the first flower appearing in September 1967. The uniform growth and productivity of this plant, the classic opening form of its flowers, and the lovely shell pink flower coloring led to my propagating the plant by grafting at Richmond, Ind. Successive propagations of this plant by grafting, at Richmond, Ind., and by budding at Livermore, Calif., have demonstrated that its distinguishing characteristics appear to be firmly fixed and hold true from generation to generation.

DESCRIPTION OF THE DRAWING

My new variety of rose plant is illustrated by the accompanying photographic drawing which shows, in full color, typical specimens of bud in several stages of opening, a face view of a newly opened flower and a face view of a flower opened for three days, upper and under sides of mature leaves, and mature and young specimens of the wood. The colors shown are as true as it is reasonably possible to obtain by means of conventional photographic procedures.

DESCRIPTION OF THE NEW PLANT

The following is a detailed description of my new variety of rose plant with the color designations as determined by reference to the Royal Horticultural Society Colour Chart and Robert S. Wilson's Horticultural Colour Chart, each as published by The Royal Horticultural Society at London, England, and identified herein as (RHS) and (W), respectively, and the Nickerson Color Fan, specified as (N).

The plant

Origin: Seedling (identified as #27–68PS).

Parentage:

*Seed parent.*—Undisseminated seedling #19–64PS.

*Pollen parent.*—Seventeen (P.P. 1,765).

Classification: Floribunda.

Type: Greenhouse culture—for cut flowers.

Form: Bush.

Growth: Vigorous and moderately free.

Habit: Upright and much branched.

Canes: Small to medium diameter.

Main stems: Color—Green 137B (RHS).

*Thorns.*—Several, short to medium length, disposed straight to slightly downward and having a short and narrow base. Color: Greyed-Orange 165C (RHS).

*Hairs and prickles.*—None.

Branches: Color—Yellow-Green 146A (RHS) to Green 137C (RHS).

*Thorns.*—Several, short to medium in length, appearing straight to slightly downward and having a short narrow base. Color: Greyed-Orange 165B shaded to 165C (RHS).

*Hairs and prickles.*—None.

Foliage: Abundant.

*Leaves.*—Compound—odd pinnate. Size: Medium.

*Leaflets.*—3 to 7, normally 7. Shape: Oval with cuspidate apex, obtuse to slightly cordate base, and serrate margin. Color: Young Leaves: Upper surface—Greyed-Purple 183A (RHS). Under surface—Greyed-Purple 184B shaded to 184A (RHS). Mature Leaves: Upper surface—Slightly lighter than Yellow-Green 147A (RHS). Under surface—Greyed-Green 191B (RHS).

*Rachis.*—Light to medium. Upper Side: Grooved, moderately prickly. Under Side: Thorny with some pickles.

*Stipules.*—Long, moderately narrow, with points which are moderately short to medium in length and which turn out at an angle greater than 45°.

The bud

Size: Medium small, before calyx breaks and as first petal opens.

Form:

*Before calyx breaks.*—Short pointed to slightly flat, with conspicuous neck, and with foliaceous appendages on bud surface with slender bristle-like foliaceous parts extending beyond the bud tip a distance equal to ¼ to ½ or more of the bud length.

*As first petal opens.*—Bud is short pointed.

Color:

*Before calyx breaks.*—Yellow-Green 146A shaded to Yellow-Green 144A (RHS) at center of base.

*As calyx breaks.*—Outside petal color is shaded from Orange-Red 35A to 35B (RHS) with base of Yellow-Green 154C (RHS).

*As first petal opens.*—Outside petals—Red 37A with a base of Yellow-Green 154D (RHS). Inside petals—Orange-Red 35B with base of Yellow-Green 154D (RHS).

Character of opening: In greenhouse the bud opens up well. In hot, dry weather the opening bud will have a slight decrease in size and a slightly lighter color intensity.

Peduncle: Of medium length, with small to medium diameter, medium strong and very erect.

*Bark.*—Almost smooth. Color: Yellow-Green 146B (RHS).

*Thorns.*—None.

*Prickles.*—Few. Color: Translucent at top, shaded to lighter than Grey-Purple 185D (RHS) at base.

*Hairs.*—Few. Color: Shaded from Yellow-Green 150D (RHS) to translucent.

The flower

Blooming habit: Free and continuous in greenhouse.

Size: Medium, when fully opened, 3 to 3½ inches in diameter.

Form: High centered at first, with petals tightly rolled outward. Remaining high centered but with center petals more open and rolled slightly outward at maturity.

Borne: Several to a stem on moderately strong stems of medium length.

Petalage: Very double, with 28 to 36 petals arranged regularly.

*Shape.*—Outside and intermediate petals—Oval to ovate with cuspidate apex Inside petals—Obovate with cuspidate apex.

*Texture.*—Moderately leathery.

*Appearance.*—Inside—Satiny. Outside—Flat and only slightly satiny.

Color: The colors described may be modified by being shaded with other colors.

The following is the color description of a newly opened rose grown in greenhouse at Richmond, Ind., and bloomed in January 1973.

*Outside petals.*—Outer surface—Red 50D shaded to Red 49D (RHS) with a base of Green-Yellow 1D (RHS). Inside surface—Red 39D shaded to Red 36C (RHS) with a base of Yellow 2D (RHS).

*Intermediate petals.* — Outer surface — Red 38D shaded to Red 36D (RHS) with a base of Yellow-Green 154D (RHS). Inside surface—Red 38B (RHS) with a base of Green-Yellow 1A (RHS).

*Inner Petals.*—Outer surface—Red 36A with a base of Yellow 4D (RHS). Inside surface—Orange Red 33D with a base of Yellow 4C (RHS).

The following is the color description of a rose that was open for three days in greenhouse at Richmond, Ind., in November 1973.

*Outside petals.*—Outer surface—Shaded from Red 49C to Red 49D (RHS) with a base of Yellow 4D (RHS). Inside surface—Shaded from Red 50D to Red 49B (RHS) with a base of Yellow-Green 154D (RHS).

*Intermediate petals.*—Outer surface—Shaded from Red 38C to Red 38D (RHS) with a base shaded from Yellow 4C to Yellow 4D (RHS). Inside surface—Red 38C with a base of Yellow 4A (RHS).

*Inner petals.*—Outer surface—Shaded from Shell Pink 516/3 (W) to Shell Pink 516/2 (W). Inside surface—Shaded from Shell Pink 516 (W) to Shell Pink 516/1 (W).

*General color effect.*—Newly opened flower—Shell Pink 516 (W). Three days open flower—Shell Pink 516/2 (W).

Sepals: Permanent and of medium length.

*Color.*—Inside—White pubescence underlain with Yellow-Green 147C (RHS). Outside—Shaded from Yellow-Green 145B at base to Yellow-Green 146B (RHS).

Fragrance: Slightly spicy.

Persistence: Petals hang on and dry.

Effect of weather: In hot, dry weather the petals fade to Pale Pink 2.5R9/3 (N).

Lasting quality: Seven days at living room temperature (observed in October).

Reproductive organs

Stamens: Medium in number, regularly arranged about pistils and generally tucked in calyx in a single row.

*Filaments.*—Of short and medium length, most with anthers. Color: Shaded from Yellow 4C to Yellow 4D (RHS) at base then to Red 47C (RHS) at tip.

*Anthers.*—Small, most all open at once. Color: Vary from Yellow-Green 154C to Red 47B (RHS).

*Pollen.*—Moderate. Color: Orange 26A (RHS).

Pistils: Medium number.

*Styles.*—Fairly even, of medium length, moderately thin, bunched and columnar. Color: Shaded from Yellow-Green 150D (RHS) to almost translucent at base and to Red 47C (RHS) at tip.

*Stigma.*—Vary in color from Yellow-Orange 16C to Yellow-Orange 16D (RHS).

Ovaries: Some protruding from calyx.

Hips: Short, ovoid, with a conspicuous neck, gourd shaped and very smooth with thin walls.

*Color.*—Shaded from Orange 24A to Orange 24B (RHS).

Seeds: Few and very small.

My new variety of rose plant is an improvement over its seed parent in that the new plant has a much more uniform growth and improved productivity. The new variety is superior to its pollen parent Seventeen in opening form and as a finished flower. The new plant has a classic opening form that develops into a fine flower when fully opened.

In making the cross to develop this new variety, I sought to improve the flower opening and finished flower of Seventeen while retaining the color and plant renewal qualities of Seventeen and in this respect the said objectives appear to have been accomplished.

My new variety is a shell pink floribunda with classic opening form and excellent vase life as a cut flower and the flower is complemented by excellent foliage and uniformity of growth.

I claim:

1. A new and distinct variety of rose plant substantially as herein shown and described, characterized by its continuous production of fine shell pink blossoms on strong stems which have an improved opening form and vase life.

No references cited.

ROBERT E. BAGWILL, Primary Examiner